US006074844A

United States Patent [19]

Hillman et al.

[11] Patent Number: 6,074,844

[45] Date of Patent: Jun. 13, 2000

[54] POLYNUCLEOTIDES ENCODING HUMAN MEMBRANE FUSION PROTEINS

[75] Inventors: Jennifer L. Hillman, Mountain View; Preeti Lal, Sunnyvale; Neil C. Corley, Mountain View, all of Calif.

[73] Assignee: Incyte Pharmaceuticals, Inc., Palo Alto, Calif.

[21] Appl. No.: 08/872,979

[22] Filed: Jun. 11, 1997

[51] Int. Cl.[7] .......................... C12N 15/12; C12N 15/63; C12N 15/85

[52] U.S. Cl. .................... 435/69.1; 435/325; 435/252.3; 435/320.1; 536/23.5; 536/23.1

[58] Field of Search ................................ 536/23.4, 23.5, 536/23.1; 435/69.1, 325, 252.3, 320.1

[56] References Cited

PUBLICATIONS

Ferro–Novick, S., et al., "Vesicle fusion from yeast to man", *Nature,* 370: 191–193 (1994).

Sudhof, T.C., "The synaptic vesicle cycle: a cascade of protein–protein interactions", *Nature,* 375: 645–653 (1995).

Sudhof, T.C., et al., "Synaptotagmins: C2–Domain Proteins That Regulate Membrane Traffic", *Neuron,* 17: 379–388 (1996).

Ibaraki, K., et al., "Identification of Four Different Forms of Syntaxin 3", *Biochem Biophys Res Commun,* 211: 997–1005 (1995), No Seq ID[5] submitted.

Perin, M.S., et al., "Structural and Functional Conservation of Synaptotagmin (p65) in *Drosophila* and Humans", *J. Biol. Chem.,* 266: 615–622 (1991), No. Seq ID[5] submitted.

Smirnova, T., et al., "Assignment of the Human Syntaxin 1b Gene (STX) to Chromosome 16p11.2 by Fluorescence in Situ Hybridization", *Genomics,* 36: 551–553 (1996).

Vincent A., et al., "Autoimmunity to the voltage–gated calcium channel underlies the Lambert–Eaton myasthenic syndrome, a paraneoplastic disorder", *Trends Neurosci,* 12:496–502 (1989).

Hay, J.C., et al, "Protein Interactions Regulating Vesicle Transport Between the Endoplasmic Reticulum and Golgi Apparatus in Mammalian Cells", *Cell,* 89: 149–158 (1997).

Schulze K.L., et al., "Drosophila syntaxin Is Required for Cell Viability and My Function in Membrane Formation and Stabilization" *Genetics,* 144: 1713–1724 (1996).

Li, C., et al., "$Ca^{2+}$–dependent and –independent activities of neural and non–neural synaptotagmins", *Nature,* 375: 594–599 (1995).

Morimoto, T., et al., "Calcium–Dependent Transmitter Secretion from Fibroblasts: Modulation by Synaptotagmin I.", *Neuron,* 15; 689–696 (1995).

Rudinger In "Peptide Hormones" (Jun. 1976) ed. J.A. Parson, University Park Press, Baltimore, pp. 1–7.

Hillier et al., Gen Bank database, Accession No. AA167677 (Dec. 1996).

Hillier et al., Gen Bank database, Accession No. R21569 (Apr. 1995).

Hillier et al, Gen Bank database, Accession No. H 72013 (Oct. 1995).

Hillier et al., Gen Bank database, Accession No. R83217 (Aug. 1995).

Hillier et al., Gen Bank database, Accession No. H72014 (Oct. 1995).

Li et al., Gen Bank database, Accession Nos. U20107 and U20110 (Feb. 1996).

*Primary Examiner*—Paula K. Hutzell
*Assistant Examiner*—Robert C. Hayes
*Attorney, Agent, or Firm*—Sheela Mohan-Peterson; Leanne C. Price; Incyte Pharmaceuticals, Inc.

[57] ABSTRACT

The invention provides two new human membrane fusion proteins (SYTAX1 or SYTAX2) and polynucleotides which identify and encode SYTAX1 or SYTAX2. The invention also provides expression vectors, host cells, agonists, antibodies and antagonists. The invention also provides methods for treating disorders associated with expression of SYTAX1 or SYTAX2.

14 Claims, 15 Drawing Sheets

```
                9                  18                 27                 36                 45                 54
TGT AGA GCG AGC AGG TCT CAG CTC CTC GTC ATG TCA TAC GGT CCC TTA GAC ATG
                                        M   S   Y   G   P   L   D   M

                63                 72                 81                 90                 99                108
TAC CGG AAC CCG GGG CCC TCG GGG CCC CAG CTC CGG GAC TTC AGC AGC ATC ATC
Y   R   N   P   G   P   S   G   P   Q   L   R   D   F   S   S   I   I

               117                126                135                144                153                162
CAG ACG TGC AGC GGC AAC ATC CAG CGG ATC AGC CAA GCC ACT GCT CAG ATA AAG
Q   T   C   S   G   N   I   Q   R   I   S   Q   A   T   A   Q   I   K

               171                180                189                198                207                216
AAT TTG ATG AGC CAG CTA GGA ACT AAG CAG GAC TCA AGC AAG CTA CAG GAA AAT
N   L   M   S   Q   L   G   T   K   Q   D   S   S   K   L   Q   E   N

               225                234                243                252                261                270
CTG CAA CAG TTA CAA CAC TCC ACA AAT CAG CTC GCC AAG GAA ACA AAT GAA TTG
L   Q   Q   L   Q   H   S   T   N   Q   L   A   K   E   T   N   E   L

               279                288                297                306                315                324
CTG AAA GAA TTA GGG TCC TTG CCC CTT CCC TTA TCT ACT TCA GAA CAG CGC CAG
L   K   E   L   G   S   L   P   L   P   L   S   T   S   E   Q   R   Q

               333                342                351                360                369                378
CAG AGA CTT CAG AAG GAA CGC CTC ATG AAT GAC TTC TCT GCA GCC TTA AAC AAT
Q   R   L   Q   K   E   R   L   M   N   D   F   S   A   A   L   N   N
```

FIGURE 1A

```
                387                 396                 405                 414                 423                 432
TTC  CAG  GCT  GTG  CAG  AGA  AGG  GTA  TCT  GAA  AAG  GAA  AAG  GAG  AGT  ATT  GCC  AGA
F    Q    A    V    Q    R    R    V    S    E    K    E    K    E    S    I    A    R

                441                 450                 459                 468                 477                 486
GCA  AGA  GCT  GGA  TCT  CGT  CTT  TCT  GCA  GAA  GAG  AGG  CAA  AGA  GAG  GAG  CAG  CTG
A    R    A    G    S    R    L    S    A    E    E    R    Q    R    E    E    Q    L

                495                 504                 513                 522                 531                 540
GTC  TCA  TTT  GAC  AGC  CAT  GAG  GAG  TGG  AAC  CAG  ATG  CAG  AGC  CAG  GAG  GAT  GAG
V    S    F    D    S    H    E    E    W    N    Q    M    Q    S    Q    E    D    E

                549                 558                 567                 576                 585                 594
GTG  GCC  ATC  ACT  GAG  CAG  GAT  TTG  GAA  CTT  ATT  AAA  GAA  AGA  GAA  ACG  GCA  ATT
V    A    I    T    E    Q    D    L    E    L    I    K    E    R    E    T    A    I

                603                 612                 621                 630                 639                 648
CGG  CAG  CTG  GAG  GCT  GAC  ATT  TTG  GAT  GTC  AAT  CAG  ATA  TTT  AAA  GAT  TTG  GCC
R    Q    L    E    A    D    I    L    D    V    N    Q    I    F    K    D    L    A

                657                 666                 675                 684                 693                 702
ATG  ATG  ATC  CAT  GAC  CAG  GGT  GAT  CTG  ATT  GAT  AGC  ATA  GAA  GCC  AAT  GTG  GAA
M    M    I    H    D    Q    G    D    L    I    D    S    I    E    A    N    V    E

                711                 720                 729                 738                 747                 756
AGC  TCA  GAG  GTG  CAC  GTC  GAA  AGA  GCC  ACT  GAA  CAG  TTA  CAG  CGA  GCT  GCT  TAC
S    S    E    V    H    V    E    R    A    T    E    Q    L    Q    R    A    A    Y
```

FIGURE 1B

```
        765         774         783         792         801         810
TAT CAG AAA AAA TCT CGC AAG AAG ATG TGT ATC CTG GTG CTT GTC CTG TCA GTG
Y   Q   K   K   S   R   K   K   M   C   I   L   V   L   V   L   S   V

        819         828         837         846         855         864
ATT ATT CTA ATC TTG GGA CTT ATT ATC TGG CCA GTT TAT AAA ACG AAG TGC TTG
I   I   L   I   L   G   L   I   I   W   P   V   Y   K   T   K   C   L

        873         882         891         900         909         918
CCT CCG ATC GTT CTC CCG CTG AGC TGT TTT CAA GGG CAA GTG CTT GTT GAA GTC
P   P   I   V   L   P   L   S   C   F   Q   G   Q   V   L   V   E   V

        927         936         945         954         963         972
TTG CCA GAA CAA ACT GAT CAC AAG AAG ACA GCA TAT ATC AGA ACG TCC TGT AAT
L   P   E   Q   T   D   H   K   K   T   A   Y   I   R   T   S   C   N

        981         990         999        1008        1017        1026
CAT TTA GTT AGA AAC TAA CTA CTA ACT AGT CTT TGG AAT TCG TGA CCT ATG GAG
H   L   V   R   N

       1035        1044        1053        1062        1071        1080
ACA GTA ATT ATC AAT TTA TTG ATT CTA TTG ATT TCT CAA ATT AGG AAT TAA CTT

       1089        1098        1107        1116        1125        1134
ACG CGG ACT TCC GTC CCT CTT CGA ATT CTG CTC GGC CTT CAC TCC AAG GGT TTA
```

FIGURE 1C

```
     1143           1152           1161           1170           1179      1188
CCC GAA ATC CCA TCC CAG CAA CTC TTG GCT TCG CAC ATG GCC CTA GCG CCC AGT

     1197           1206           1215           1224           1233      1242
AAA ATC TGC CTA CCA CGC AAA CCA CAA TTT CCC TCT TCC ACA GCA CCC GAG CAT

     1251           1260
CAG CCA CCC CCC GGC ACC ACG GAA C
```

```
1    M S - - Y G P L D M - - - Y R N P G P S - - - - G P Q L R D F S S - - - - I I Q   1363873
1    M - - - - - - - - - - Q L T Q D D D T D A V E I A I D N T A F M D E F F S E I E   GI 1143494
1    M K D R L E Q L K A K Q L T Q D D D T D E V E I A I D N T A F M D E F F S E I E   GI 924268

28   T C S G N I Q R I S Q A T A Q I K N L M S Q L - G T K Q D S S K L Q E N L Q Q L   1363873
31   E T R L N I D K I S E H V E E A K K L Y S I I L S A P I P E P K T K D D L E Q L   GI 1143494
41   E T R L N I D K I S E H V E E A K K L Y S I I L S A P I P E P K T K D D L E Q L   GI 924268

67   Q H S T N Q L A K E T N E L L K E L G - - - S L P L P L S T S E Q R Q Q R L Q K   1363873
71   S T E I K K R A N N V R N K L K S M E K H I E E D E V R S S A D L R I R K S Q H   GI 1143494
81   T T E I K K R A N N V R N K L K S M E K H I E E D E V R S S A D L R I R K S Q H   GI 924268

104  E R L M N D F S A A L N N F Q A V Q R R V S E K E K E S I A R A R A G S R L S A   1363873
111  S V L S R K F V E V M T K Y N E A Q V D F R E R S K G R I - - - - - - - - - - -   GI 1143494
121  S V L S R K F V E V M T K Y N E A Q V D F R E R S K G R I - - - - - - - - - - -   GI 924268

144  E E R Q R E E Q L V S F D S H E E W N Q M Q S Q E D E V - - - A I T E Q D L E L   1363873
140  - Q R Q L E I T G K K T T D E E L E E M L E S G N P A I F T S G I I D S Q I S K   GI 1143494
150  - Q R Q L E I T G K K T T D E E L E E M L E S G N P A I F T S G I I D S Q I S K   GI 924268

181  - - - - - I K E R E T A I R Q L E A D I L D V N Q I F K D L A M M I H D Q G D L   1363873
179  Q A L S E I E G R H K D I V R L E S S I K E L H D M F M D I A M L V E N Q G E M   GI 1143494
189  Q A L S E I E G R H K D I V R L E S S I K E L H D M F M D I A M L V E N Q G E M   GI 924268
```

```
216 I D S I E A N V E S S E V H V E R A T E Q L Q R A A Y Y Q K K S R K K M C I L V 1363873
219 L D N I E L N V M H T V D H V E K A R D E S K K A V K Y Q S Q A R K K L I I I I GI 1143494
229 L D N I E L N V M H T V D H V E K A R D E T K R A M K Y Q G Q A R K K L I I I I GI 924268

256 L V L S V I I L I L G L I I W P V Y K T K C L P P I V L P L S C F Q G Q V L V E 1363873
259 V L V V V L L G I L A L I I - - - - - - - - - - G L S V G L - - - - - - - - - - GI 1143494
269 V V V V V L L G I L A L I I - - - - - - - - - - G L S V G L - - - - - - - - - - GI 924268

296 V L P E Q T D H K K T A Y I R T S C N H L V R N 1363873
279 - - - - - - - - - - - - - - - - - - - - - - - N GI 1143494
289 - - - - - - - - - - - - - - - - - - - - - - - K GI 924268
```

```
                9           18          27          36          45          54
ATG GGG CAC CCA CCA GTC TCT CCC AGT GCC CCG GCC CCA GCT GGC ACC ACA GCT
M   G   H   P   P   V   S   P   S   A   P   A   P   A   G   T   T   A

                63          72          81          90          99          108
ATA CCT GGG CTT ATT CCA GAC CTT GTC GCC GGG ACC CCC TGG CCC CGC TGG GCT
I   P   G   L   I   P   D   L   V   A   G   T   P   W   P   R   W   A

                117         126         135         144         153         162
CTC ATT GCC GGC GCC CTT GCC GCG GGC GTC CTC CTC GTC TCC TGC CTC CTC TGT
L   I   A   G   A   L   A   A   G   V   L   L   V   S   C   L   L   C

                171         180         189         198         207         216
GCT GCC TGC TGC TGC TGC CGC CGC CAC AGG AAG AAG CCC AGG GAC AAG GAG TCC
A   A   C   C   C   C   R   R   H   R   K   K   P   R   D   K   E   S

                225         234         243         252         261         270
GTG GGT CTG GGC AGT GCC CGC GGC ACC ACC ACC ACC CAC CTG GTG CAA CCT GAT
V   G   L   G   S   A   R   G   T   T   T   T   H   L   V   Q   P   D

                279         288         297         306         315         324
GTG GAT GGC CTG GAG TCC AGC CCG GGG GAT GCT CAG CAA TGG GGG CGC CTG CAG
V   D   G   L   E   S   S   P   G   D   A   Q   Q   W   G   R   L   Q

                333         342         351         360         369         378
CTC TCC CTG GAG TTC GAC TTT GGA AGC CAG GAG ATC AGG GTG GGC CTG AGG CAG
L   S   L   E   F   D   F   G   S   Q   E   I   R   V   G   L   R   Q
```

FIGURE 4A

```
        387         396         405         414         423         432
GCA GCC GAC CTG ATG CCT GGG GGC ACC GTG GAC CCC TAT GCC CGG GTC AGC GTC
A   A   D   L   M   P   G   G   T   V   D   P   Y   A   R   V   S   V

        441         450         459         468         477         486
TCC ACC CAG GCC GGA CAC AGA CAT GAG ACA AAA GTG CAC CGA GGC ACG CTC TGC
S   T   Q   A   G   H   R   H   E   T   K   V   H   R   G   T   L   C

        495         504         513         522         531         540
CCC GTG TTT GAC GAG ACC TGC TGC TTC CAC ATC CCG CAG GCG GAG CTG CCA GGG
P   V   F   D   E   T   C   C   F   H   I   P   Q   A   E   L   P   G

        549         558         567         576         585         594
GCC ACC CTG CAG GTG CAG CTT TTC AAC TTC AAG CGC TTC TCG GGG CAT GAG CCC
A   T   L   Q   V   Q   L   F   N   F   K   R   F   S   G   H   E   P

        603         612         621         630         639         648
CTG GGT GAG CTC CGT CTG GCA CTG GGC ACC GTG GAT CTG CAG CAT GTT CTG GAG
L   G   E   L   R   L   A   L   G   T   V   D   L   Q   H   V   L   E

        657         666         675         684         693         702
CAC TGG TAC CTG CTG GGC CCG CCG GCT GCC ACT CAG CCC GAG CAG GTC GGG GAG
H   W   Y   L   L   G   P   P   A   A   T   Q   P   E   Q   V   G   E

        711         720         729         738         747         756
CTG TGC TTC TCT CTC CGG TAC GTG CCC AGC TCA GGC CGG CTG ACC GTG GTG GTG
L   C   F   S   L   R   Y   V   P   S   S   G   R   L   T   V   V   V
```

FIGURE 4B

```
                765                 774                 783                 792                 801                 810
CTG GAG GCT CGA GGC CTG CGT CCA GGA CTT GCA GAG CCC TAC GTG AAG GTC CAG
L   E   A   R   G   L   R   P   G   L   A   E   P   Y   V   K   V   Q

                819                 828                 837                 846                 855                 864
CTC ATG CTG AAC CAG AGG AAG TGG AAG AAG AGA AAG ACA GCC ACC AAA AAG GGC
L   M   L   N   Q   R   K   W   K   K   R   K   T   A   T   K   K   G

                873                 882                 891                 900                 909                 918
ACG GCG GCC CCC TAC TTC AAT GAG GCC TTC ACC TTC CTG GTG CCC TTC AGC CAG
T   A   A   P   Y   F   N   E   A   F   T   F   L   V   P   F   S   Q

                927                 936                 945                 954                 963                 972
GTC CAG AAT GTG GAC CTG GTG CTG GCT GTC TGG GAC CGC AGC CTG CCG CTC CGA
V   Q   N   V   D   L   V   L   A   V   W   D   R   S   L   P   L   R

                981                 990                 999                1008                1017                1026
ACT GAG CCC GTA GGC AAG GTG CAC CTG GGT GCC CGG GCC TCG GGG CAG CCC CTG
T   E   P   V   G   K   V   H   L   G   A   R   A   S   G   Q   P   L

               1035                1044                1053                1062                1071                1080
CAG CAC TGG GCA GAC ATG CTG GCC CAC GCA GCC AGG GAG GTG GAC CGC ATG CTG
Q   H   W   A   D   M   L   A   H   A   A   R   E   V   D   R   M   L

               1089                1098                1107                1116                1125                1134
GCC CTG CAG CCC CGC CTT CGC CTG CGC CTG CCC TTG CCC CAC TCC TGA ATG CAC
A   L   Q   P   R   L   R   L   R   L   P   L   P   H   S
```

FIGURE 4C

```
       1143      1152      1161      1170      1179      1188
CAC ATG CCT CTG TCT CCC CGC TGA GCC CAG GCA CTT GCC CAG GCC GCC CTG CAG

       1197      1206
GAC CAC TGC AAT AAA CGC C
```

```
1    M - - - - - - - - - G H P P V S - - - - - - - - - - - - P S A P A P A G T T A I   1003941
1    - - - - - - - - - - - - - - - - - - - - - - - - - - - - - - - - - - - - - - - -   GI 643658
1    M V S E S H H E A L A A P P V T T V A T V L P S N A T E P A S P G E G K E D A F   GI 338658

20   P G L I P D L V A G - - - T P W P R W A L I A G A L A A G V L L V S C L L C A A   1003941
1    - - - - - - - - - - - - - - - - P R W T L F I A I L A A G V L L V S C L L C V I   GI 643658
41   S K L K E K F M N E L H K I P L P P W A L I A I A I V A V L L V L T C C F C I -   GI 338658

57   C C C C R - R H R - - K K P R D K - - - E S V G L G S A R G T T T T - - - - H L   1003941
25   C C Y C H - R H R H R K Q P K D K - - - E T V G L G S A R N S T T T - - - - H L   GI 643658
80   C K K C L F K K K N K K K G K E K G G K N A I N M K D V K D L G K T M K D Q A L   GI 338658

87   V Q P D V D - G L E S S - - - - - P G D A Q Q W G R L Q L S L E F D F G S Q E I   1003941
57   V Q P D V D - C L E P C - - - - - S G G D Q Q W G R L L L S L E Y D F G S Q E I   GI 643658
120  K D D D A E T G L T D G E E K E E P K E E E K L G K L Q Y S L D Y D F Q N N Q L   GI 338658

121  R V G L R Q A A D L M P - - - G G T V D P Y A R V S V S T Q A G H R H E T K V H   1003941
91   R V G L R Q A G N L K A - - - E G T A D P Y A W V S V S T Q S G R R H E T K V H   GI 643658
160  L V G I I Q A A E L P A L D M G G T S D P Y V K V F L L P D K K K K F E T K V H   GI 338658

158  R G T L C P V F D E T C C F H I P Q A E L P G A T L Q V Q L F N F K R F S G H E   1003941
128  R G T L S P M F E E T C C F L V P P A E L P K A T L K V Q L W D F K R F S E H E   GI 643658
200  R K T L N P V F N E Q F T F K V P Y S E L G G K T L V M A V Y D F D R F S K H D   GI 338658
```

```
198 P L G E L R L A L G T V D L Q H V L E H W Y L L G P P A A T Q P E Q V G E L C F 1003941
168 P L G E L Q L P L G T V D L Q H V L E S W Y Q L G P P G T T E P E Q M G E L C F GI 643658
240 I I G E F K V P M N T V D F G H V T E E W R D L Q S A E K E E Q E K L G D I C F GI 338658

238 S L R Y V P S S G R L T V V V L E A R G L R P - - - - G L A E P Y V K V Q L M L 1003941
208 S L R Y V P S S G S L T V V V L E A R G L N P - - - - G L A E A Y V K I Q L M L GI 643658
280 S L R Y V P T A G K L T V V I L E A K N L K K M D V G G L S D P Y V K I H L M Q GI 338658

274 N Q R K W K K R K T A T K K G T A A P Y F N E A F T F L V P F S Q V Q N V D L V 1003941
244 N Q R K W K K S K T S S K K G T T T P Y F N E A F V F L V P V S Q L Q S V D L V GI 643658
320 N G K R L K K K K T T I K K N T L N P Y Y N E S F S F E V P F E Q I Q K V Q V V GI 338658

314 L A V W D R S L P L R T E P V G K V H L G A R A S G Q P L Q H W A D M L A H A - 1003941
284 L A V W A R G L Q L R T E P V G K V L L G S R A S G Q P L Q H W A D M L A H A R GI 643658
360 V T V L D Y D K I G K N D A I G K V F V G Y N S T G A E L R H W S D M L A N P R GI 338658

353 - - - - - - - - - - - - - A R E V D R M L A L Q P R L R L R L P L P H S 1003941
324 R P I A Q W H H L R S P R E V D R V L A L Q P R L P L - L R - P R S GI 643658
400 R P I A Q W H T L Q V E E E V D A M L A V - - - - - - - - - - - - K K GI 338658
```

POLYNUCLEOTIDES ENCODING HUMAN MEMBRANE FUSION PROTEINS

FIELD OF THE INVENTION

This invention relates to nucleic acid and amino acid sequences of two new human membrane fusion proteins and to the use of these sequences in the diagnosis, prevention, and treatment of cancer and neuronal disorders.

BACKGROUND OF THE INVENTION

Membrane vesicle fusion in eukaryotic cells is a highly regulated process coordinated through complexes of specific proteins. A variety of essential cellular functions, including protein transport and secretion, membrane protein distribution, and synaptic transmission, depend on regulated vesicle fusion. Many of the components which mediate the docking, priming, and fusion of membrane vesicles have been identified and characterized using mammalian synaptic nerve terminals as a model system. Homologues of these synaptic vesicle fusion proteins are located throughout the cell in the regions where intracellular membranes undergo fusion (Ferro-Novick, S., and Jahn, R. (1994) Nature 370:191–193).

In the nerve terminal, synaptic vesicles are tightly docked in specific locations near calcium channels on the presynaptic plasma membrane. During docking, synaptic vesicle proteins specifically complex with plasma membrane molecules, and this complex acts as a scaffold for the assembly of the fusion apparatus. The vesicle associated membrane protein binds to the plasma membrane syntaxin and SNAP-25 proteins. Once this trimeric core has assembled, it serves as a receptor for the cytosolic proteins α-SNAP and NSF. The ATPase activity of NSF then primes the synaptic vesicle-membrane complex for a calcium influx which will lead to vesicle fusion and extrusion of the vesicle contents.

When the nerve terminal is depolarized, $Ca^{2+}$ enters via voltage-gated $Ca^{2+}$ channels. High local concentrations of $Ca^{2+}$ trigger the fusion of docked vesicles with the plasma membrane, which releases neurotransmitters into the synaptic cleft. A calcium-binding molecule, synaptotagmin, completes the process by interacting with syntaxin (Sudhof, T. C. (1995) Nature 375:645–653).

At least nine isoforms of synaptotagmin are expressed in brain and other organs. The members of this family are integral membrane proteins that span the vesicle membrane once and have a short amino-terminal intravesicular domain and a large cytoplasmic domain. The cytoplasmic domain contains two repeats homologous to the calcium-binding C2 domains found in $Ca^{2+}$-dependent isoforms of protein kinase C. Characterization of human and Drosophila synaptotagmins shows a selective conservation of C2 domains between the species. Nuclear magnetic resonance spectroscopy and site-directed mutagenesis showed that the interaction of synaptotagmin and syntaxin is mediated by the action of basic residues surrounding the $Ca^{2+}$-binding sites of the synaptotagmin C2A domain with the abundant acidic residues of the syntaxin molecule. Additionally, synaptotagmin specifically interacts with the cytoplasmic domains of neurexins, which are involved in many aspects of synapse organization. Inactivation of syntaxin and synaptotagmin with botulinum neurotoxin causes flaccid paralysis. (Sudhof, T. C. and Rizo, J. (1996) Neuron 17: 379–388; Ibaraki, K. et al. (1995) Biochem. Biophys. Res. Commun. 211:997–1005; and Perin, M. S. et al. (1991) J. Biol. Chem. 266:615–622).

The syntaxins display a broad tissue distribution, participate in vesicle docking with the presynaptic plasma membrane and in the regulated secretion of molecules, such as insulin, and regulate the potential targeting and fusion of carrier vesicles following export from the ER. Members of this family contain an N-terminal region exposed to the cytoplasm and C-terminal hydrophobic residues believed to function as a membrane anchor. The human syntaxin 1B gene has been mapped to 16p11.2 by fluorescence in situ hybridization. Chromosome rearrangements with breaks in 16p11 are observed in myxoid liposarcoma and in acute myeloid leukemia. Small cell lung cancer, a tumor that displays neuroendocrine properties, has been observed in about 60% of patients with Lambert-Eaton myasthenic syndrome, an autoimmune disease of neurotransmission that is characterized by muscle weakness. Analysis of Drosophila syntaxin mutants indicates that syntaxin is required for cell viability and may mediate membrane assembly events throughout development (Smimova, T. et al. (1996) Genomics 36: 551–553; Vincent et al. (1989) Trends Neurosci. 12:496–502; Hay, J. C. et al. (1997) Cell 89:149–158; and Schulze, K. L. and Bellen, H. J. (1996) Genetics 144:1713–1724).

The discovery of two new human membrane fusion proteins and the polynucleotides encoding them satisfies a need in the art by providing new compositions which are useful in the diagnosis, prevention and treatment of cancer and neuronal disorders.

SUMMARY OF THE INVENTION

The invention features two substantially purified polypeptides, new human membrane fusion proteins (collectively designated SYTAX and individually, SYTAX1 and SYTAX2), having the amino acid sequences shown in SEQ ID NO:1 and SEQ ID NO:3 or fragments thereof, respectively.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding SYTAX1 under conditions suitable for the expression of the polypeptide; and b) recovering the polypeptide from the host cell culture.

The invention also provides a pharmaceutical composition comprising a substantially purified SYTAX1 having the amino acid sequence of SEQ ID NO:1 in conjunction with a suitable pharmaceutical carrier.

The invention also provides a purified antagonist which decreases the activity of a polypeptide of SEQ ID NO:1. In one aspect the invention provides a purified antibody which binds to a polypeptide comprising at least a fragment of the amino acid sequence of SEQ ID NO:1.

Still further, the invention provides a purified agonist which modulates the activity of the polypeptide of SEQ ID NO:1.

The invention also provides a method for treating or preventing cancer comprising administering to a subject in need of such treatment an effective amount of an antagonist which decreases the activity of SYTAX1.

The invention also provides a method for treating or preventing neuronal disorders comprising administering to a subject in need of such treatment an effective amount of an antagonist which decreases the activity of SYTAX1.

The invention also provides a method for detecting a polynucleotide which encodes SYTAX1 in a biological sample comprising the steps of: a) hybridizing a polynucleotide sequence complementary to the polynucleotide which encodes SEQ ID NO:1 to nucleic acid material of a biological sample, thereby forming a hybridization complex; and b) detecting the hybridization complex, wherein the presence of the complex correlates with the presence of a polynucleotide encoding SYTAX1 in the biological sample. In a preferred embodiment, prior to hybridization, the nucleic acid material of the biological sample is amplified by the polymerase chain reaction.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4.

In another aspect the invention provides a composition comprising an isolated and purified polynucleotide sequence comprising the complement of SEQ ID NO:4, or fragments or variants thereof. The invention also provides a polynucleotide sequence comprising the complement of SEQ ID NO:4.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding SYTAX2 under conditions suitable for the expression of the polypeptide; and b) recovering the polypeptide from the host cell culture.

The invention also provides a pharmaceutical composition comprising a substantially purified SYTAX2 having the amino acid sequence of SEQ ID NO:3 in conjunction with a suitable pharmaceutical carrier.

The invention also provides a purified antagonist which decreases the activity of a polypeptide of SEQ ID NO:3. In one aspect the invention provides a purified antibody which binds to a polypeptide comprising at least a fragment of the amino acid sequence of SEQ ID NO:3.

Still further, the invention provides a purified agonist which modulates the activity of the olypeptide of SEQ ID NO:3.

The invention also provides a method for treating or preventing cancer comprising administering to a subject in need of such treatment an antagonist which decreases the activity of SYTAX2.

The invention also provides a method for treating or preventing neuronal disorders comprising administering to a subject in need of such treatment an effective amount of an antagonist which decreases the activity of SYTAX2.

The invention also provides a method for detecting a polynucleotide which encodes SYTAX1 in a biological sample comprising the steps of: a) hybridizing a polynucleotide sequence complementary to the polynucleotide which encodes SEQ ID NO:3 to nucleic acid material of a biological sample, thereby forming a hybridization complex; and b) detecting the hybridization complex, wherein the presence of the complex correlates with the presence of a polynucleotide encoding SYTAX2 in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of SYTAX1. The alignment was produced using MacDNASIS PRO™ software (Hitachi Software Engineering Co. Ltd. San Bruno, Calif.).

FIGS. 2A and 2B show the amino acid sequence alignments among SYTAX1 (SEQ ID NO:1), human syntaxin (GI 1143494; SEQ ID NO:5), and mouse syntaxin (GI 924268; SEQ ID NO:6), produced using the multisequence alignment program of DNASTAR™ software (DNASTAR Inc, Madison Wis.).

FIGS. 4A, 4B, 4C, and 4D show the amino acid sequence (SEQ ID NO:3) and nucleic acid sequence (SEQ ID NO:4) of SYTAX2. The alignment was produced using MacDNASIS PRO™ software (Hitachi Software Engineering Co. Ltd. San Bruno, Calif.).

FIGS. 5A and 5B show the amino acid sequence alignments among SYTAX2 (SEQ ID NO:3), mouse synaptotagmin (GI 643658; SEQ ID NO:7), and human synaptotagmin (GI 338658; SEQ ID NO:8), produced using the multisequence alignment program of DNASTAR™ software (DNASTAR Inc, Madison Wis.).

DESCRIPTION OF THE INVENTION

Figure 3A:
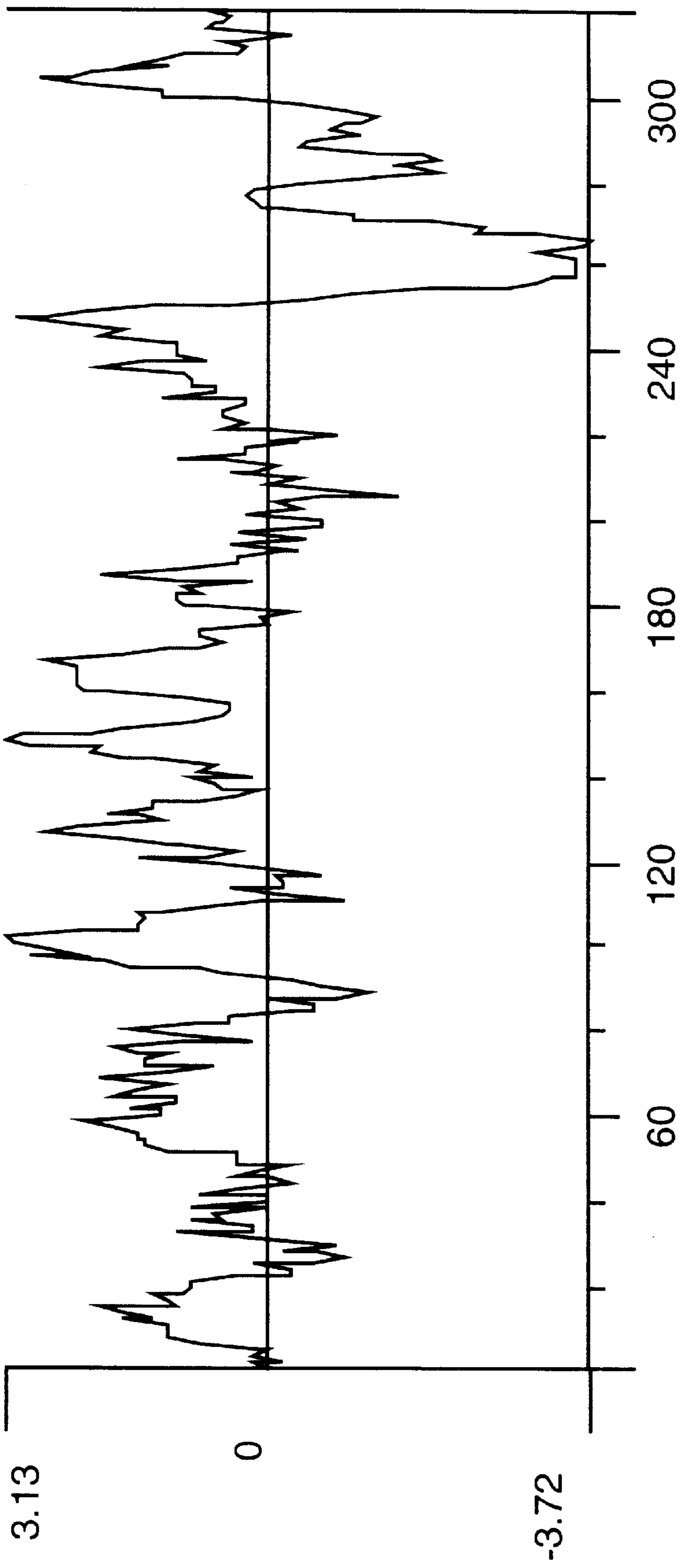
FIGS. 3A, 3B and 3C show the hydrophobicity plots for SYTAX1, (SEQ ID NO:1), human syntaxin (GI 1143494; SEQ ID NO:5), and mouse syntaxin (GI 924268; SEQ ID NO:6) (SEQ ID NO:3), respectively; the positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

SYTAX, as used herein, refers to the amino acid sequences of substantially purified SYTAX obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to SYTAX, increases or prolongs the duration of the effect of SYTAX. Agonists may include proteins, nucleic acids, carbohydrates, or any other molecules which bind to and modulate the effect of SYTAX.

An "allele" or "allelic sequence", as used herein, is an alternative form of the gene encoding SYTAX. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding SYTAX as used herein include those with deletions, insertions, or substitutions of different nucleotides resulting in a polynucleotide that encodes the same or a functionally equivalent SYTAX. Included within this definition are polymorphisms which may or may not be readily detectable using a particular oligonucleotide probe of the polynucleotide encoding SYTAX, and improper or unexpected hybridization to alleles, with a locus other than the normal chromosomal locus for the polynucleotide sequence encoding SYTAX. The encoded protein may also be "altered" and contain deletions, insertions, or substitutions of amino acid residues which produce a silent change and result in a functionally equivalent SYTAX. Deliberate amino acid substitutions may be made on the basis of similarity in polarity, charge, solubility, hydrophobicity, hydrophilicity, and/or the amphipathic nature of the residues as long as the biological or immunological activity of SYTAX is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of SYTAX are preferably about 5 to about 15 amino acids in length and retain the biological activity or the immunological activity of SYTAX. Where "amino acid sequence" is recited herein to refer to an amino acid sequence of a naturally occuring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to SYTAX, decreases the amount or the duration of the effect of the biological or immunological activity of SYTAX. Antagonists may include proteins, nucleic acids, carbohydrates, or any other molecules which decrease the effect of SYTAX.

As used herein, the term "antibody" refers to intact molecules as well as fragments thereof, such as Fab, $F(ab')_2$, and Fv, which are capable of binding the epitopic determinant. Antibodies that bind SYTAX polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic SYTAX, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding SYTAX (SEQ ID NO:1 or SEQ ID NO:3) or fragments thereof (e.g., SEQ ID NO:2 or SEQ ID NO:4 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding SYTAX in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to SYTAX or the encoded SYTAX. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct oligonucleotides synthesized on a substrate, such as paper, nylon or other type of membrane, filter, chip, glass slide, or any other suitable solid support.

The term “modulate”. as used herein, refers to a change in the activity of SYTAX. For example, modulation may cause an increase or a decrease in protein activity, binding characteristics, or any other biological, functional or immunological properties of SYTAX.

“Nucleic acid sequence” as used herein refers to an oligonucleotide, nucleotide, or polynucleotide, and fragments thereof, and to DNA or RNA of genomic or synthetic origin which may be single- or double-stranded, and represent the sense or antisense strand. “Fragments” are those nucleic acid sequences which are greater than 60 nucleotides than in length, and most preferably includes fragments that are at least 100 nucleotides or at least 1000 nucleotides, and at least 10,000 nucleotides in length.

The term “oligonucleotide” refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms “amplimers”,“primers”, “oligomers”, and “probes”, as commonly defined in the art.

“Peptide nucleic acid”, PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term “portion”, as used herein, with regard to a protein (as in “a portion of a given protein”) refers to fragments of that protein. The fragments may range in size from five amino acid residues to the entire amino acid sequence minus one amino acid. Thus, a protein “comprising at least a portion of the amino acid sequence of SEQ ID NO:1” encompasses the full-length SYTAX and fragments thereof.

The term “sample”, as used herein, is used in its broadest sense. A biological sample suspected of containing nucleic acid encoding SYTAX, or fragments thereof, or SYTAX itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms “specific binding” or “specifically binding”, as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope “A”, the presence of a protein containing epitope A (or free, unlabeled A) in a reaction containing labeled “A” and the antibody will reduce the amount of labeled A bound to the antibody.

The terms “stringent conditions” or “stringency”, as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term “substantially purified”, as used herein, refers to nucleic or amino acid sequences that are removed from their natural environment, isolated or separated, and are at least 60% free, preferably 75% free, and most preferably 90% free from other components with which they are naturally associated.

A “substitution”, as used herein, refers to the replacement of one or more amino acids or nucleotides by different amino acids or nucleotides, respectively.

“Transformation”, as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such “transformed” cells include stably transformed cells in which the inserted DNA is capable of replication either as an autonomously replicating plasmid or as part of the host chromosome. They also include cells which transiently express the inserted DNA or RNA for limited periods of time.

A “variant ” of SYTAX, as used herein, refers to an amino acid sequence that is altered by one or more amino acids. The variant may have “conservative” changes, wherein a substituted amino acid has similar structural or chemical properties, e.g., replacement of leucine with isoleucine. More rarely, a variant may have “nonconservative” changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of two new human membrane fusion proteins (hereinafter referred to as SYTAX1 and SYTAX2, and collectively, as SYTAX), the polynucleotides encoding SYTAX, and the use of these compositions for the diagnosis, prevention, or treatment of cancer and neuronal disorders.

Nucleic acids encoding the SYTAX1 of the present invention were first identified in Incyte Clone 1363873 from the lung tissue cDNA library (LUNGNOT12) using a computer search for amino acid sequence alignments. A consensus sequence, SEQ ID NO:2, was derived from the following overlapping and/or extended nucleic acid sequences: Incyte Clones 1363873, (LUNGNOT12) and 2444583 (THP1NOT03).

Figure 3B:
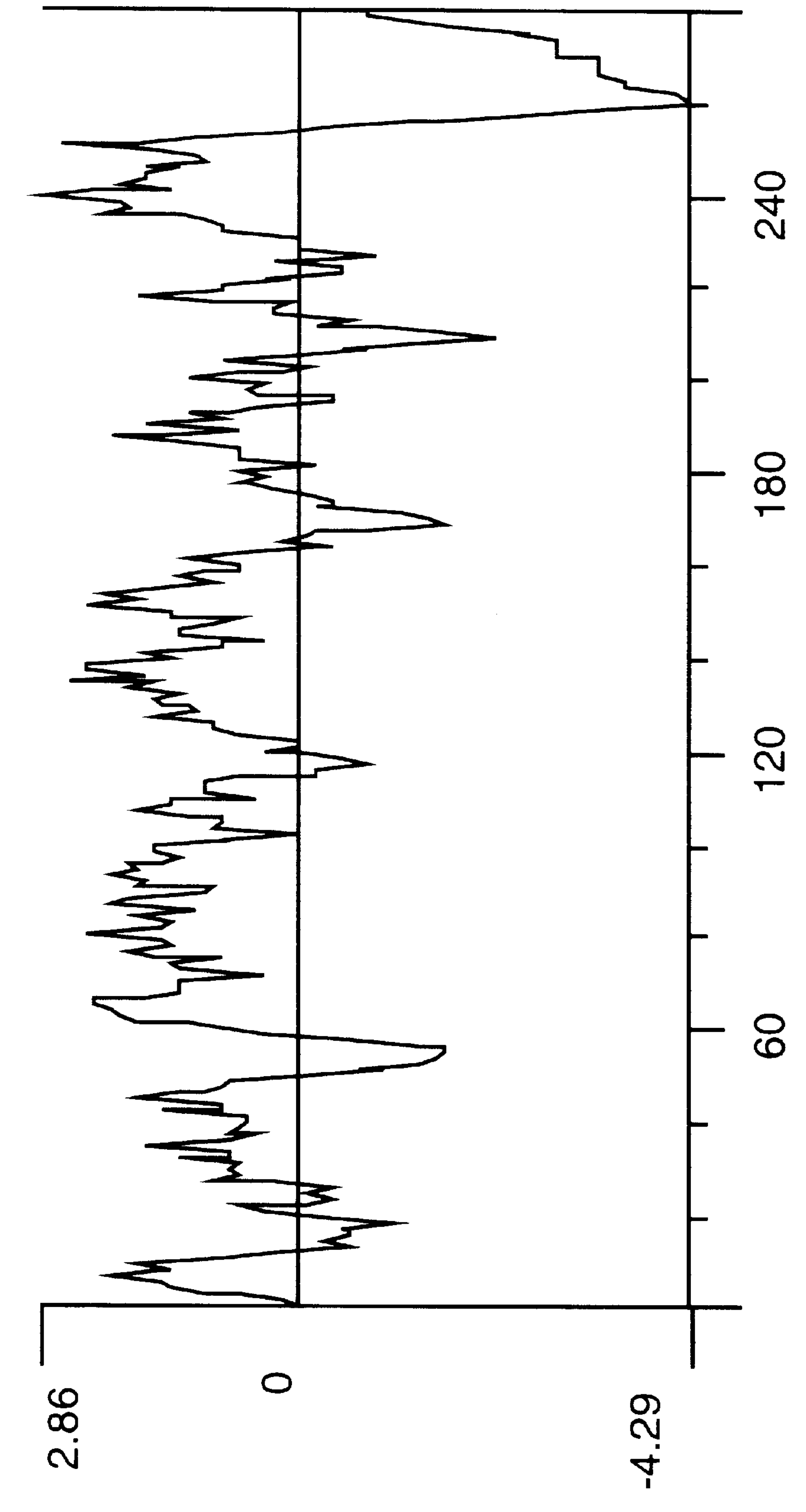
Figure 3C:
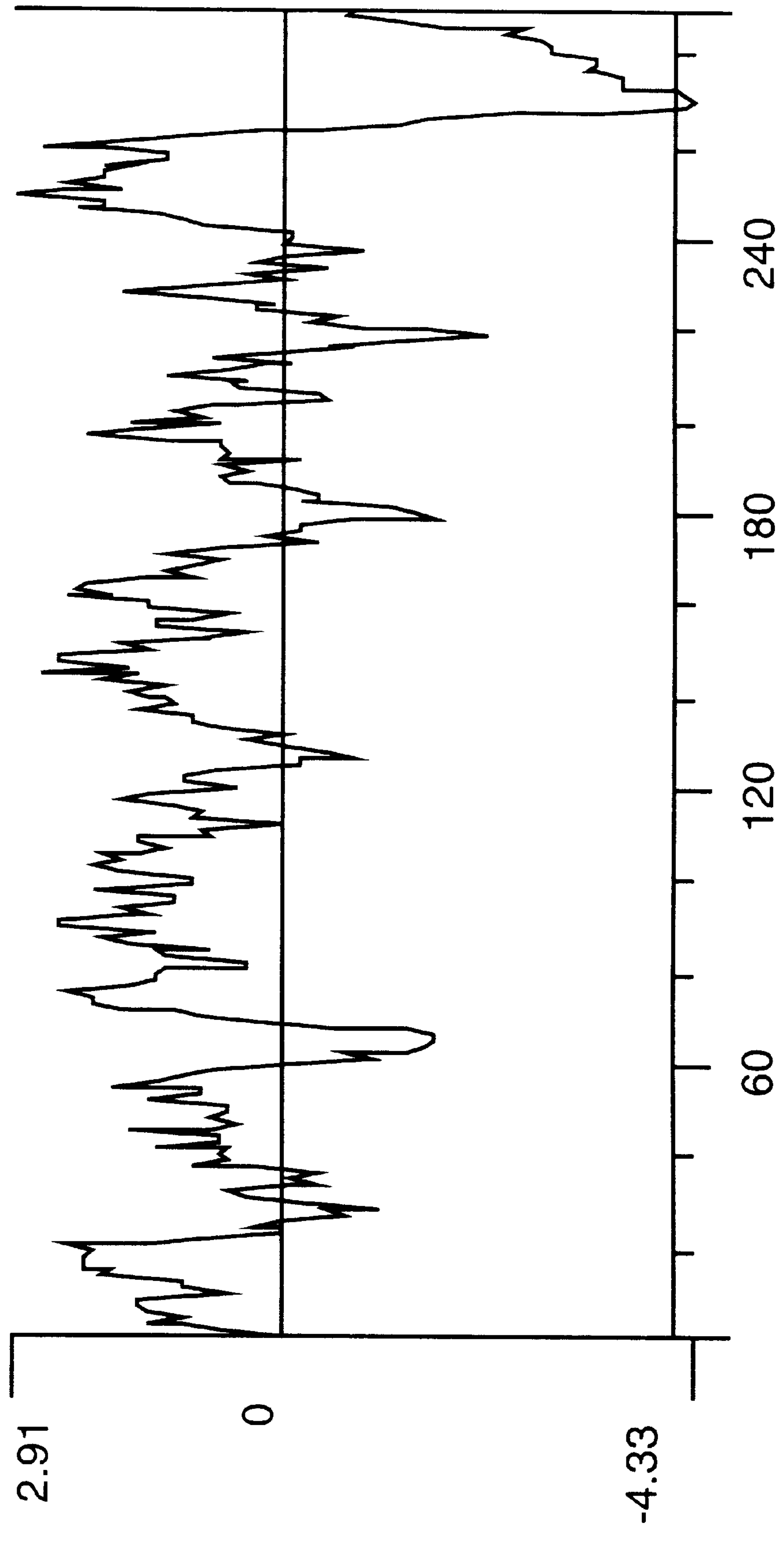

In one embodiment, the invention encompasses a polypeptide comprising the amino acid sequence of SEQ ID NO:1, as shown in FIG. 1. SYTAX1 is 319 amino acids in length. As shown in FIGS. 2A and 2B, SYTAX1 has chemical and structural homology with human syntaxin (GI 1143494; SEQ ID NO:5) and mouse syntaxin (GI 924268; SEQ ID NO:6). In particular, SYTAX1 and human syntaxin share 21% identity, while SYTAX1 and mouse syntaxin share 22% identity. As illustrated by FIGS. 3A, 3B, and 3C, SYTAX1, mouse syntaxin, and human syntaxin have rather similar hydrophobicity plots. Northern analysis shows the expression of this sequence in various libraries, at least 60% of which are immortalized or cancerous.

Nucleic acids encoding SYTAX2 of the present invention were first identified in Incyte Clone 1003941 from the breast tissue cDNA library (BRSTNOT03) using a computer search for amino acid sequence alignments. A consensus sequence, SEQ ID NO:3, was derived from the following overlapping and/or extended nucleic acid sequences: Incyte Clones 1003941, (LUNGNOT12), and 1701574 (BLADTUT05).

In one embodiment, the invention encompasses a polypeptide comprising the amino acid sequence of SEQ ID NO:3, as shown in FIGS. 4A, 4B, 4C, and 4D. SYTAX2 is 375 amino acids in length and has a potential tramsmembrane region from residues T30 to $C_{57}$. As shown in FIGS. 5A and 5B, SYTAX2 has chemical and structural homology with mouse synaptotagmin (GI 643658; SEQ ID NO:7) and human synaptotagmin (GI 338658; SEQ ID NO:7). In particular, SYTAX2 and mouse synaptotagmin share 73% identity, and SYTAX2 and human synaptotagmin share 41% identity. Northern analysis shows the expression of this sequence in various libraries, at least 63% of which are immortalized or cancerous.

The invention also encompasses SYTAX variants. A preferred SYTAX variant is one having at least 80%, and more preferably 90%, amino acid sequence identity to the SYTAX amino acid sequence (SEQ ID NO:1 or SEQ ID NO:3). A most preferred SYTAX variant is one having at least 95% amino acid sequence identity to SEQ ID NO:1 or SEQ ID NO:3.

The invention also encompasses polynucleotides which encode SYTAX. Accordingly, any nucleic acid sequence which encodes the amino acid sequence of SYTAX can be used to produce recombinant molecules which express SYTAX. In a particular embodiment, the invention encompasses the polynucleotides comprising the nucleic acid sequence of SEQ ID NO:2 as shown in FIGS. 1A, 1B, 1C, and 1D, and the nucleic acid sequence of SEQ ID NO:4 as shown in FIGS.4A, 4B, 4C, and 4D.

It will be appreciated by those skilled in the art that as a result of the degeneracy of the genetic code, a multitude of nucleotide sequences encoding SYTAX, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring SYTAX, and all such variations are to be considered as being specifically disclosed.

Although nucleotide sequences which encode SYTAX and their variants are preferably capable of hybridizing to the nucleotide sequence of the naturally occurring SYTAX under appropriately selected conditions of stringency, it may be advantageous to produce nucleotide sequences encoding SYTAX or their derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ABBR and their derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode SYTAX and their derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding SYTAX or any fragment thereof.

Also encompassed by the invention are polynucleotide sequences that are capable of hybridizing to the claimed nucleotide sequences, and in particular, those shown in SEQ ID NO 2 or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding SYTAX may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode SYTAX may be used in recombinant DNA molecules to direct expression of SYTAX, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express SYTAX.

As will be understood by those of skill in the art, it may be advantageous to produce SYTAX-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter SYTAX encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding SYTAX may be ligated to a heterologous sequence to encode a fusion protein. For example, to screen peptide libraries for inhibitors of SYTAX activity, it may be useful to encode a chimeric SYTAX protein that can be recognized by a commercially available antibody. A fusion protein may also be engineered to contain a cleavage site located between the SYTAX encoding sequence and the heterologous protein sequence, so that SYTAX may be cleaved and purified away from the heterologous moiety.

In another embodiment, sequences encoding SYTAX may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of SYTAX, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of SYTAX, or any part thereof, may be altered during direct synthesis and/or combined using chemical methods with sequences from other proteins, or any part thereof, to produce a variant polypeptide.

In order to express a biologically active SYTAX, the nucleotide sequences encoding SYTAX or functional equivalents, may be inserted into appropriate expression vector, i.e., a vector which contains the necessary elements for the transcription and translation of the inserted coding sequence.

Methods which are well known to those skilled in the art may be used to construct to expression vectors containing sequences encoding SYTAX and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding SYTAX. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSportl™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding SYTAX, vectors based on SV40 or EBV may be used with an appropriate selectable marker.

In bacterial systems, a number of expression vectors may be selected depending upon the use intended for SYTAX. For example, when large quantities of SYTAX are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding SYTAX may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding SYTAX may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express SYTAX. For example, in one such system, *Autographa californica* nuclear polyhedrosis virus (AcNPV) is used as a vector to express foreign genes in *Spodoptera frugiperda* cells or in Trichoplusia larvae. The sequences encoding SYTAX may be cloned into a non-essential region of the virus, such as the polyhedrin gene, and placed under control of the polyhedrin promoter. Successful insertion of SYTAX will render the polyhedrin gene inactive and produce recombinant virus lacking coat protein. The recombinant viruses may then be used to infect, for example, *S. frugiperda* cells or Trichoplusia larvae in which SYTAX may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding SYTAX may be ligated into an adenovirus transcription/translation complex consisting of the late promoter and tripartite leader sequence. Insertion in a non-essential E1 or E3 region of the viral genome may be used to obtain a viable virus which is capable of expressing SYTAX in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding SYTAX. Such signals include the ATG initiation codon and adjacent sequences. In cases where sequences encoding SYTAX, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express SYTAX may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (llartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding SYTAX is inserted within a marker gene sequence, transformed cells containing sequences encoding SYTAX can be identified by the absence of marker gene function. Alternatively, a marker gene can be placed in tandem with a sequence encoding SYTAX under the control of a single promoter. Expression of the marker gene in response to induction or selection usually indicates expression of the tandem gene as well.

Alternatively, host cells which contain the nucleic acid sequence encoding SYTAX and express SYTAX may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding SYTAX can be detected by DNA—DNA or DNA-RNA hybridization or amplification using probes or fragments or fragments of polynucleotides encoding SYTAX. Nucleic acid amplification based assays involve the use of oligonucleotides or oligomers based on the sequences encoding SYTAX to detect transformants containing DNA or RNA encoding SYTAX.

A variety of protocols for detecting and measuring the expression of SYTAX, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on SYTAX is preferred, but a competitive binding assay may be employed. These and other assays are described, among other places, in Hampton, R. et al. (1990*; Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding SYTAX include oligolabeling, nick translation, end-labeling or PCR amplification using a labeled nucleotide. Alternatively, the sequences encoding SYTAX, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding SYTAX may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode SYTAX may be designed to contain signal sequences which direct secretion of SYTAX through a prokaryotic or eukaryotic cell membrane. Other constructions may be used to join sequences encoding SYTAX to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinaffinity purification system (Immunex Corp., Seattle, Wash.). The inclusion of cleavable linker sequences such as those specific for Factor XA or enterokinase (Invitrogen, San Diego, Calif.) between the purification domain and SYTAX may be used to facilitate purification. One such expression vector provides for expression of a fusion protein containing SYTAX and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying SYTAX from the fusion protein. A discussion of vectors which contain fusion proteins is provided in Kroll, D. J. et al. (1993; DNA Cell Biol. 12:441–453).

In addition to recombinant production, fragments of SYTAX may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of SYTAX may be chemically synthesized separately and combined using chemical methods to produce the full length molecule.

Therapeutics

Chemical and structural homology exits among SYTAX1, human syntaxin (GI 1143494), and mouse syntaxin (GI 924268). In addition, SYTAX1 is expressed in cancers and transformed cells. Diminished expression of SYTAX1 may be associated with defects in neurotransmitter vesicle transport Therefore, SYTAX1 appears to play a role in cancer and neurological disorders.

Therefore, in one embodiment, antagonists which decrease the activity of SYTAX1 may be administered to a subject to prevent or treat cancer. Such cancers may include, but are not limited to, adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind SYTAX1 may be used directly as an antagonist or indirectly as a targeting or delivery mechanism for bringing a pharmaceutical agent to cells or tissue which express SYTAX1. In one aspect, antibodies which specifically bind SYTAX1 may be used directly as an antagonist or indirectly as a targeting or delivery mechanism for bringing a pharmaceutical agent to cells or tissue which express SYTAX1.

In another embodiment, a vector expressing the complement of the polynucleotide encoding SYTAX1 may be administered to a subject to treat or prevent cancer, and in particular, those cancers described above.

In another embodiment, SYTAX1 or a fragment or derivative thereof may be administered to a subject to treat or prevent a neuronal disorders. Such neuronal disorders include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

In another embodiment, a vector expressing the polynucleotide encoding SYTAX1 may be administered to a subject to treat or prevent neuronal disorders, and in particular, the neuronal disorders described above.

In another embodiment, an agonist which modulates the activity of SYTAX1 may also be administered to a subject to treat or prevent a neuronal disorders, and in particular, the neuronal disorders described above.

Chemical and structural homology exits among SYTAX2, mouse synaptotagmin (GI 643658), and human synaptotagmin (GI 338658). In addition, SYTA2 is expressed in cancers and transformed cells. Diminished expression of SYTAX2 may be associated with defects in neurotransmitter vesicle transport Therefore, SYTAX2 appears to play a role in cancer and neurological disorders.

Therefore, in one embodiment, antagonists which decrease the activity of SYTAX2 may be administered to a subject to prevent or treat cancer. Such cancers may include, but are not limited to, adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind SYTAX2 may be used directly as an antagonist or indirectly as a targeting or delivery mechanism for bringing a pharmaceutical agent to cells or tissue which express SYTAX2. In one aspect, antibodies which specifically bind SYTAX2 may be used directly as an antagonist or indirectly as a targeting or delivery mechanism for bringing a pharmaceutical agent to cells or tissue which express SYTAX2.

In another embodiment, a vector expressing the complement of the polynucleotide encoding SYTAX2 may be administered to a subject to treat or prevent cancer, and in particular, those cancers described above.

In another embodiment, a vector expressing the complement of the polynucleotide encoding SYTAX2 may be administered to a subject to treat or prevent cancer, and in particular, the cancers disorders described above.

In another embodiment, SYTAX2 or a fragment or derivative thereof may be administered to a subject to treat or prevent a neuronal disorders. Such neuronal disorders include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

In another embodiment, a vector expressing the polynucleotide encoding SYTAX1 may be administered to a subject to treat or prevent neuronal disorders, and in particular, the neuronal disorders described above.

In another embodiment, an agonist which modulates the activity of SYTAX1 may also be administered to a subject to treat or prevent a neuronal disorders, and in particular, the neuronal disorders described above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of SYTAX may be produced using methods which are generally known in the art. In particular, purified SYTAX may be used to produce antibodies or to screen libraries of pharmaceutical agents to identify those which specifically bind SYTAX.

Antibodies to SYTAX may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with SYTAX or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to SYTAX have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of SYTAX amino acids may be fused with those of another protein such as keyhole limpet hemocyanin and antibody produced against the chimeric molecule.

Monoclonal antibodies to SYTAX may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce SYTAX-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for SYTAX may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between SYTAX and its specific antibody. A two-site, monoclonal-based immunoassay utilizing monoclonal antibodies reactive to two non-interfering SYTAX epitopes is preferred, but a competitive binding assay may also be employed (Maddox, supra).

In another embodiment of the invention, the polynucleotides encoding SYTAX, or any fragment or complement thereof, may be used for therapeutic purposes. In one aspect, the complement of the polynucleotide encoding SYTAX may be used in situations in which it would be desirable to block the transcription of the mRNA. In particular, cells may be transformed with sequences complementary to polynucleotides encoding SYTAX. Thus, complementary molecules or fragments may be used to modulate SYTAX activity, or to achieve regulation of gene function. Such technology is now well known in the art, and sense or antisense oligonucleotides or larger fragments, can be designed from various locations along the coding or control regions of sequences encoding SYTAX.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding SYTAX. These techniques are described both in Sambrook et al. (supra) and in Ausubel et al. (supra).

Genes encoding SYTAX can be turned off by transforming a cell or tissue with expression vectors which express high levels of a polynucleotide or fragment thereof which encodes SYTAX. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding SYTAX (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding SYTAX.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding SYTAX. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of SYTAX, antibodies to SYTAX, mimetics, agonists, antagonists, or inhibitors of SYTAX. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of SYTAX, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example SYTAX or fragments thereof, antibodies of SYTAX, agonists, antagonists or inhibitors of SYTAX, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind SYTAX may be used for the diagnosis of conditions or diseases characterized by expression of SYTAX, or in assays to monitor patients being treated with SYTAX, agonists, antagonists or inhibitors. The antibodies useful for diagnostic purposes may be prepared in the same manner as those described above for therapeutics. Diagnostic assays for SYTAX include methods which utilize the antibody and a label to detect SYTAX in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring SYTAX are known in the art and provide a basis for diagnosing altered or abnormal levels of SYTAX expression. Normal or standard values for SYTAX expression are established by combining body fluids or cell extracts taken from normal mammalian subjects, preferably human, with antibody to SYTAX under conditions suitable for complex formation The amount of standard complex formation may be quantified by various methods, but preferably by photometric, means. Quantities of SYTAX expressed in subject, control and disease, samples from biopsied tissues are compared with the standard values. Deviation between standard and subject values establishes the parameters for diagnosing disease.

In another embodiment of the invention, the polynucleotides encoding SYTAX may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of SYTAX may be correlated with disease. The diagnostic assay may be used to distinguish between absence, presence, and excess expression of SYTAX, and to monitor regulation of SYTAX levels during therapeutic intervention.

In one aspect, hybridization with PCR probes which are capable of detecting polynucleotide sequences, including genomic sequences, encoding SYTAX or closely related molecules, may be used to identify nucleic acid sequences which encode SYTAX. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding SYTAX, alleles, or related sequences.

Probes may also be used for the detection of related sequences, and should preferably contain at least 50% of the nucleotides from any of the SYTAX encoding sequences. The hybridization probes of the subject invention may be DNA or RNA and derived from the nucleotide sequence of SEQ ID NO 2 or SEQ ID NO:4 or from genomic sequence including promoter, enhancer elements, and introns of the naturally occurring SYTAX.

Means for producing specific hybridization probes for DNAs encoding SYTAX include the cloning of nucleic acid sequences encoding SYTAX or SYTAX derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding SYTAX may be used for the diagnosis of conditions, disorders, or diseases which are associated with expression of SYTAX. Examples of such conditions or diseases include cancers such as adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, uterus; and akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. The polynucleotide sequences encoding SYTAX may be used in Southern or northern analysis, dot blot, or other membrane-based technologies; in PCR technologies; or in dipstick, pin, ELISA assays or microarrays utilizing fluids or tissues from patient biopsies to detect altered SYTAX expression. Such qualitative or quantitative methods are well known in the art.

In a particular aspect, the nucleotide sequences encoding SYTAX may be useful in assays that detect activation or induction of various cancers, particularly those mentioned above. The nucleotide sequences encoding SYTAX may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding SYTAX in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of SYTAX, a normal or standard profile for expression is established. This may be accomplished by combining body fluids or cell extracts taken from normal subjects, either animal or human, with a sequence, or a fragment thereof, which encodes SYTAX, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding SYTAX may involve the use of PCR. Such oligomers may be chemically synthesized, generated enzymatically, or produced in vitro. Oligomers will preferably consist of two nucleotide sequences, one with sense orientation (5'<–3') and another with antisense (3'–>5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of SYTAX include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides derived from any of the polynucleotide sequences described herein may be used as probes in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode SYTAX may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding SYTAX on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, SYTAX, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between SYTAX and the agent being tested, may be measured.

Another technique for drug screening which may be used provides for high throughput screening of compounds having suitable binding affinity to the protein of interest as described in published PCT application WO84/03564. In this method, as applied to SYTAX large numbers of different small test compounds are synthesized on a solid substrate, such as plastic pins or some other surface. The test compounds are reacted with SYTAX, or fragments thereof, and washed. Bound SYTAX is then detected by methods well known in the art. Purified SYTAX can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding SYTAX specifically compete with a test compound for binding SYTAX. In this manner, the antibodies can be used to detect the presence of any peptide which shares one or more antigenic determinants with SYTAX.

In additional embodiments, the nucleotide sequences which encode SYTAX may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

BRSTNOT03

The BRSTNOT03 cDNA library was constructed from breast tissue removed from a 54-year-old Caucasian female (specimen #0025B; Mayo Clinic, Rochester, N.Y.) who had undergone bilateral radical mastectomy following diagnosis of residual invasive grade 3 of 4 mammary ductal adenocarcinoma. The pathology report indicated that the biopsied fibroadipose tissue from the right breast was negative for tumor. Tumor cells were identified in the right breast, forming a nodule 1×0.7×0.7 cm. The remaining breast parenchyma exhibited proliferative fibrocystic changes without atypia. The skin, nipple, and fascia were uninvolved. One of 10 axillary lymph nodes was involved with metastatic tumor, as a microscopic, intranodal focus. Prior to surgery, the patient was prescribed estrogen as part of postmenopausal hormone replacement therapy.

LUNGNOT12

The LUNGNOT12 cDNA library was constructed from lung tissue obtained from a 78-year-old Caucasian male (specimen #0022A; Mayo Clinic, Rochester, Minn.) who had undergone a segmental lung resection following diagnosis of malignant neoplasm of the right upper lobe. The pathology report indicated invasive pulmonary grade 3 adenocarcinoma forming a peripheral mass with associated fibrosis. The fibrosis pleura was puckered, but not invaded. Additionally, the patient exhibited ventricular premature beats and chronic airway obstruction due to extrinsic asthma. Prior to surgery, the patient was prescribed Cipro® I.V. (ciprofloxacin administered for treatment of systemic infection; Bayer Corp., West Haven, Conn.); Atenolol (tenormin for arrhythmia; Duramed Pharmaceuticals, Inc., Cincinnati, Ohio); Naprosyn® (naproxen, an anti-inflammatory and analgesic; Roche Laboratories, Nutley, N.J.); Darvocet-N® (propoxyphene napsylate for pain; Eli Lilly and Co., Indianapolis, Ind.), and multivitamins. The patient history included the following surgeries: cholecystectomy, radical prostatectomy, and regional lymph node excision. The pathology report also indicated a history of cerebrovascular disease, arteriosclerotic vascular disease, thrombophlebitis, malignant neoplastic prostate, and previous tobacco abuse which was in remission. The patient family history included intracranial hematoma with deep coma following injury in patient's mother; and cerebrovascular disease, arteriosclerotic vascular disease, and Type I diabetes in patient's siblings.

For both libraries the frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3M sodium acetate and 2.5 volumes of ethanol, resuspended in RNAse-free water, and DNase treated at 37° C. The RNA extraction was repeated with acid phenol pH 4.0 and precipitated with sodium acetate and ethanol as before. The mRNA was then isolated using the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #27510501; Pharmacia), and those cDNAs exceeding 400 bp were ligated into pSport I. The plasmid pSport I was subsequently transformed into DH5a™ competent cells (Cat. #18258-012; Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173, QIAGEN, Inc.). The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno,Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc Nat. Acad. Sci. 90:5893–3) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for eptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a Glxxx±p (where xxx is pri, rod, etc and if present, p=peptide). Product score, the calculation of which is shown below, was used to determine the electronic stringency. For an exact match, product score was set at 70 with a conservative lower limit set at approximately 40 (1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding SYTAX occurs. Abundance and percent abundance are also reported. Abundance directly reflects the number of times a particular transcript is represented in a cDNA library, and percent abundance is abundance divided by the total number of sequences examined in the cDNA library.

V Extension of SYTAX Encoding Polynucleotides

The nucleic acid sequence of Incyte Clone 1363873 or Incyte Clone 1003941 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2×Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO 2 or SEQ ID NO:4 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO 2 or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 $\mu$Ci of [$\gamma$-$^{32}P$] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the SYTAX-encoding sequence, or any part thereof, is used to decrease or inhibit expression of naturally occurring SYTAX. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of SYTAX, SEQ ID NO 1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the SYTAX-encoding transcript.

IX Expression of SYTAX

Expression of SYTAX is accomplished by subcloning the cDNAs into appropriate vectors and transforming the vectors into host cells. In this case, the cloning vector is also used to express SYTAX in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of SYTAX into the bacterial growth media which can be used directly in the following assay for activity.

X Demonstration of SYTAX Activity

SYTAX activity is tested using a vector which contains the nucleotide sequence for SYTAX or purified SYTAX protein. The vector or protein is introduced into CHO fibroblasts in culture using methods known in the art. Following endocytic uptake of acetylcholine (ACh), CHO fibroblasts exhibit Ca(2+)-dependent spontaneous quantal ACh release and depolarization-evoked ACh release, as detected by a whole-cell voltage-clamped myocyte in contact with the fibroblast. CHO fibroblasts transfected with SYTAX will show a change in the spontaneous quantal ACh release and an enhanced Ca(2+)-evoked ACh release, as compared with control cells (Morimoto, T., et al., (1995) Neuron 15: 689–696).

XI Production of SYTAX Specific Antibodies

SYTAX that is substantially purified using PAGE electrophoresis (Sambrook, supra), or other purification techniques, is used to immunize rabbits and to produce antibodies using standard protocols. The amino acid sequence deduced from SEQ ID NO 2 or SEQ ID NO:4 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring SYTAX Using Specific Antibodies

Naturally occurring or recombinant SYTAX is substantially purified by immunoaffinity chromatography using antibodies specific for SYTAX. An immunoaffinity column is constructed by covalently coupling SYTAX antibody to an activated chromatographic resin, such as CNBr-activated Sepharose (Pharmacia & Upjohn). After the coupling, the resin is blocked and washed according to the manufacturer's instructions.

Media containing SYTAX is passed over the immunoaffinity column, and the column is washed under conditions that allow the preferential absorbance of SYTAX (e.g., high ionic strength buffers in the presence of detergent). The column is eluted under conditions that disrupt antibody/SYTAX binding (eg, a buffer of pH 2–3 or a high concentration of a chaotrope, such as urea or thiocyanate ion), and SYTAX is collected.

XIII Identification of Molecules Which Interact with SYTAX

SYTAX or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled SYTAX, washed and any wells with labeled SYTAX complex are assayed. Data obtained using different concentrations of SYTAX are used to calculate values for the number, affinity, and association of SYTAX with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO:1.

2. An isolated and purified polynucleotide which is completely complementary to the polynucleotide of claim 1.

3. An expression vector comprising the polynucleotide of claim 1.

4. A host cell comprising the expression vector of claim 3.

5. A method for producing a polypeptide comprising the amino acid sequence of SEQ ID NO:1, the method comprising the steps of:

a) culturing the host cell of claim 4 under conditions suitable for the expression of the polypeptide; and b) recovering the polypeptide from the host cell culture.

6. An isolated and purified polynucleotide comprising SEQ ID NO:2.

7. A polynucleotide which is completely complementary to the polynucleotide of claim 6.

8. An isolated and purified polynucleotide encoding a polypeptide comprising the amino acid sequence of SEQ ID NO:3.

9. An isolated and purified polynucleotide which is completely complementary to the polynucleotide of claim 8.

10. An expression vector comprising the polynucleotide of claim 8.

11. A host cell comprising the expression vector of claim 10.

12. A method for producing a polypeptide comprising the amino acid sequence of SEQ ID NO:3, the method comprising the steps of:

a) culturing the host cell of claim 11 under conditions suitable for the expression of the polypeptide; and b) recovering the polypeptide from the host cell culture.

13. An isolated and purified polynucleotide comprising SEQ ID NO:4.

14. An isolated and purified polynucleotide which is completely complementary to the polynucleotide of claim 13.

* * * * *

```
                              SEQUENCE LISTING


(1) GENERAL INFORMATION:

   (iii) NUMBER OF SEQUENCES: 8


(2) INFORMATION FOR SEQ ID NO:1:

     (i) SEQUENCE CHARACTERISTICS:
          (A) LENGTH: 319 amino acids
          (B) TYPE: amino acid
          (C) STRANDEDNESS: single
          (D) TOPOLOGY: linear

   (vii) IMMEDIATE SOURCE:
          (A) LIBRARY: BRSTNOT03
          (B) CLONE: 1363873

    (xi) SEQUENCE DESCRIPTION: SEQ ID NO:1:

Met Ser Tyr Gly Pro Leu Asp Met Tyr Arg Asn Pro Gly Pro Ser Gly
 1               5                  10                  15

Pro Gln Leu Arg Asp Phe Ser Ser Ile Ile Gln Thr Cys Ser Gly Asn
            20                  25                  30

Ile Gln Arg Ile Ser Gln Ala Thr Ala Gln Ile Lys Asn Leu Met Ser
        35                  40                  45

Gln Leu Gly Thr Lys Gln Asp Ser Ser Lys Leu Gln Glu Asn Leu Gln
    50                  55                  60

Gln Leu Gln His Ser Thr Asn Gln Leu Ala Lys Glu Thr Asn Glu Leu
65                  70                  75                  80

Leu Lys Glu Leu Gly Ser Leu Pro Leu Pro Leu Ser Thr Ser Glu Gln
                85                  90                  95

Arg Gln Gln Arg Leu Gln Lys Glu Arg Leu Met Asn Asp Phe Ser Ala
            100                 105                 110

Ala Leu Asn Asn Phe Gln Ala Val Gln Arg Arg Val Ser Glu Lys Glu
        115                 120                 125

Lys Glu Ser Ile Ala Arg Ala Arg Ala Gly Ser Arg Leu Ser Ala Glu
    130                 135                 140

Glu Arg Gln Arg Glu Glu Gln Leu Val Ser Phe Asp Ser His Glu Glu
145                 150                 155                 160

Trp Asn Gln Met Gln Ser Gln Glu Asp Glu Val Ala Ile Thr Glu Gln
                165                 170                 175
```

-continued

```
Asp Leu Glu Leu Ile Lys Glu Arg Glu Thr Ala Ile Arg Gln Leu Glu
            180                 185                 190

Ala Asp Ile Leu Asp Val Asn Gln Ile Phe Lys Asp Leu Ala Met Met
        195                 200                 205

Ile His Asp Gln Gly Asp Leu Ile Asp Ser Ile Glu Ala Asn Val Glu
    210                 215                 220

Ser Ser Glu Val His Val Glu Arg Ala Thr Glu Gln Leu Gln Arg Ala
225                 230                 235                 240

Ala Tyr Tyr Gln Lys Lys Ser Arg Lys Lys Met Cys Ile Leu Val Leu
                245                 250                 255

Val Leu Ser Val Ile Ile Leu Ile Leu Gly Leu Ile Ile Trp Pro Val
            260                 265                 270

Tyr Lys Thr Lys Cys Leu Pro Pro Ile Val Leu Pro Leu Ser Cys Phe
        275                 280                 285

Gln Gly Gln Val Leu Val Glu Val Leu Pro Glu Gln Thr Asp His Lys
    290                 295                 300

Lys Thr Ala Tyr Ile Arg Thr Ser Cys Asn His Leu Val Arg Asn
305                 310                 315
```

(2) INFORMATION FOR SEQ ID NO:2:

(i) SEQUENCE CHARACTERISTICS:
(A) LENGTH: 1267 base pairs
(B) TYPE: nucleic acid
(C) STRANDEDNESS: single
(D) TOPOLOGY: linear (vii) IMMEDIATE SOURCE:
(A) LIBRARY: BRSTNOT03
(B) CLONE: 1363873

(xi) SEQUENCE DESCRIPTION: SEQ ID NO:2:

```
TGTAGAGCGA GCAGGTCTCA GCTCCTCGTC ATGTCATACG GTCCCTTAGA CATGTACCGG    60
AACCCGGGGC CCTCGGGGCC CCAGCTCCGG GACTTCAGCA GCATCATCCA GACGTGCAGC   120
GGCAACATCC AGCGGATCAG CCAAGCCACT GCTCAGATAA AGAATTTGAT GAGCCAGCTA   180
GGAACTAAGC AGGACTCAAG CAAGCTACAG GAAAATCTGC AACAGTTACA ACACTCCACA   240
AATCAGCTCG CCAAGGAAAC AAATGAATTG CTGAAAGAAT TAGGGTCCTT GCCCCTTCCC   300
TTATCTACTT CAGAACAGCG CCAGCAGAGA CTTCAGAAGG AACGCCTCAT GAATGACTTC   360
TCTGCAGCCT TAAACAATTT CCAGGCTGTG CAGAGAAGGG TATCTGAAAA GGAAAAGGAG   420
AGTATTGCCA GAGCAAGAGC TGGATCTCGT CTTTCTGCAG AAGAGAGGCA AAGAGAGGAG   480
CAGCTGGTCT CATTTGACAG CCATGAGGAG TGGAACCAGA TGCAGAGCCA GGAGGATGAG   540
GTGGCCATCA CTGAGCAGGA TTTGGAACTT ATTAAAGAAA GAGAAACGGC AATTCGGCAG   600
CTGGAGGCTG ACATTTTGGA TGTCAATCAG ATATTTAAAG ATTTGGCCAT GATGATCCAT   660
GACCAGGGTG ATCTGATTGA TAGCATAGAA GCCAATGTGG AAAGCTCAGA GGTGCACGTC   720
GAAAGAGCCA CTGAACAGTT ACAGCGAGCT GCTTACTATC AGAAAAAATC TCGCAAGAAG   780
ATGTGTATCC TGGTGCTTGT CCTGTCAGTG ATTATTCTAA TCTTGGGACT TATTATCTGG   840
CCAGTTTATA AAACGAAGTG CTTGCCTCCG ATCGTTCTCC CGCTGAGCTG TTTTCAAGGG   900
CAAGTGCTTG TTGAAGTCTT GCCAGAACAA ACTGATCACA AGAAGACAGC ATATATCAGA   960
ACGTCCTGTA ATCATTTAGT TAGAAACTAA CTACTAACTA GTCTTTGGAA TTCGTGACCT  1020
ATGGAGACAG TAATTATCAA TTTATTGATT CTATTGATTT CTCAAATTAG GAATTAACTT  1080
ACGCGGACTT CCGTCCCTCT TCGAATTCTG CTCGGCCTTC ACTCCAAGGG TTTACCCGAA  1140
```

-continued

```
ATCCCATCCC AGCAACTCTT GGCTTCGCAC ATGGCCCTAG CGCCCAGTAA AATCTGCCTA  1200

CCACGCAAAC CACAATTTCC CTCTTCCACA GCACCCGAGC ATCAGCCACC CCCCGGCACC  1260

ACGGAAC                                                            1267
```

(2) INFORMATION FOR SEQ ID NO:3:

(i) SEQUENCE CHARACTERISTICS:
(A) LENGTH: 375 amino acids
(B) TYPE: amino acid
(C) STRANDEDNESS: single
(D) TOPOLOGY: linear (vii) IMMEDIATE SOURCE:
(A) LIBRARY: LUNGNOT12
(B) CLONE: 1003941

(xi) SEQUENCE DESCRIPTION: SEQ ID NO:3:

```
Met Gly His Pro Pro Val Ser Pro Ser Ala Pro Ala Pro Ala Gly Thr
 1               5                  10                  15

Thr Ala Ile Pro Gly Leu Ile Pro Asp Leu Val Ala Gly Thr Pro Trp
            20                  25                  30

Pro Arg Trp Ala Leu Ile Ala Gly Ala Leu Ala Ala Gly Val Leu Leu
        35                  40                  45

Val Ser Cys Leu Leu Cys Ala Ala Cys Cys Cys Cys Arg Arg His Arg
    50                  55                  60

Lys Lys Pro Arg Asp Lys Glu Ser Val Gly Leu Gly Ser Ala Arg Gly
65                  70                  75                  80

Thr Thr Thr Thr His Leu Val Gln Pro Asp Val Asp Gly Leu Glu Ser
                85                  90                  95

Ser Pro Gly Asp Ala Gln Gln Trp Gly Arg Leu Gln Leu Ser Leu Glu
            100                 105                 110

Phe Asp Phe Gly Ser Gln Glu Ile Arg Val Gly Leu Arg Gln Ala Ala
        115                 120                 125

Asp Leu Met Pro Gly Gly Thr Val Asp Pro Tyr Ala Arg Val Ser Val
    130                 135                 140

Ser Thr Gln Ala Gly His Arg His Glu Thr Lys Val His Arg Gly Thr
145                 150                 155                 160

Leu Cys Pro Val Phe Asp Glu Thr Cys Cys Phe His Ile Pro Gln Ala
                165                 170                 175

Glu Leu Pro Gly Ala Thr Leu Gln Val Gln Leu Phe Asn Phe Lys Arg
            180                 185                 190

Phe Ser Gly His Glu Pro Leu Gly Glu Leu Arg Leu Ala Leu Gly Thr
        195                 200                 205

Val Asp Leu Gln His Val Leu Glu His Trp Tyr Leu Leu Gly Pro Pro
    210                 215                 220

Ala Ala Thr Gln Pro Glu Gln Val Gly Glu Leu Cys Phe Ser Leu Arg
225                 230                 235                 240

Tyr Val Pro Ser Ser Gly Arg Leu Thr Val Val Val Leu Glu Ala Arg
                245                 250                 255

Gly Leu Arg Pro Gly Leu Ala Glu Pro Tyr Val Lys Val Gln Leu Met
            260                 265                 270

Leu Asn Gln Arg Lys Trp Lys Lys Arg Lys Thr Ala Thr Lys Lys Gly
        275                 280                 285

Thr Ala Ala Pro Tyr Phe Asn Glu Ala Phe Thr Phe Leu Val Pro Phe
    290                 295                 300

Ser Gln Val Gln Asn Val Asp Leu Val Leu Ala Val Trp Asp Arg Ser
305                 310                 315                 320
```

-continued

```
Leu Pro Leu Arg Thr Glu Pro Val Gly Lys Val His Leu Gly Ala Arg
                325                 330                 335

Ala Ser Gly Gln Pro Leu Gln His Trp Ala Asp Met Leu Ala His Ala
            340                 345                 350

Ala Arg Glu Val Asp Arg Met Leu Ala Leu Gln Pro Arg Leu Arg Leu
        355                 360                 365

Arg Leu Pro Leu Pro His Ser
    370                 375
```

(2) INFORMATION FOR SEQ ID NO:4:

(i) SEQUENCE CHARACTERISTICS:
(A) LENGTH: 1207 base pairs
(B) TYPE: nucleic acid
(C) STRANDEDNESS: single
(D) TOPOLOGY: linear (vii) IMMEDIATE SOURCE:
(A) LIBRARY: LUNGNOT12
(B) CLONE: 1003941

(xi) SEQUENCE DESCRIPTION: SEQ ID NO:4:

```
ATGGGGCACC CACCAGTCTC TCCCAGTGCC CCGGCCCCAG CTGGCACCAC AGCTATACCT    60

GGGCTTATTC CAGACCTTGT CGCCGGGACC CCCTGGCCCC GCTGGGCTCT CATTGCCGGC   120

GCCCTTGCCG CGGGCGTCCT CCTCGTCTCC TGCCTCCTCT GTGCTGCCTG CTGCTGCTGC   180

CGCCGCCACA GGAAGAAGCC CAGGGACAAG GAGTCCGTGG GTCTGGGCAG TGCCCGCGGC   240

ACCACCACCA CCCACCTGGT GCAACCTGAT GTGGATGGCC TGGAGTCCAG CCCGGGGGAT   300

GCTCAGCAAT GGGGGCGCCT GCAGCTCTCC CTGGAGTTCG ACTTTGGAAG CCAGGAGATC   360

AGGGTGGGCC TGAGGCAGGC AGCCGACCTG ATGCCTGGGG GCACCGTGGA CCCCTATGCC   420

CGGGTCAGCG TCTCCACCCA GGCCGGACAC AGACATGAGA CAAAAGTGCA CCGAGGCACG   480

CTCTGCCCCG TGTTTGACGA GACCTGCTGC TTCCACATCC CGCAGGCGGA GCTGCCAGGG   540

GCCACCCTGC AGGTGCAGCT TTTCAACTTC AAGCGCTTCT CGGGGCATGA GCCCCTGGGT   600

GAGCTCCGTC TGGCACTGGG CACCGTGGAT CTGCAGCATG TTCTGGAGCA CTGGTACCTG   660

CTGGGCCCGC CGGCTGCCAC TCAGCCCGAG CAGGTCGGGG AGCTGTGCTT CTCTCTCCGG   720

TACGTGCCCA GCTCAGGCCG GCTGACCGTG GTGGTGCTGG AGGCTCGAGG CCTGCGTCCA   780

GGACTTGCAG AGCCCTACGT GAAGGTCCAG CTCATGCTGA ACCAGAGGAA GTGGAAGAAG   840

AGAAAGACAG CCACCAAAAA GGGCACGGCG GCCCCCTACT TCAATGAGGC CTTCACCTTC   900

CTGGTGCCCT TCAGCCAGGT CCAGAATGTG GACCTGGTGC TGGCTGTCTG GGACCGCAGC   960

CTGCCGCTCC GAACTGAGCC CGTAGGCAAG GTGCACCTGG GTGCCCGGGC CTCGGGGCAG  1020

CCCCTGCAGC ACTGGGCAGA CATGCTGGCC CACGCAGCCA GGGAGGTGGA CCGCATGCTG  1080

GCCCTGCAGC CCCGCCTTCG CCTGCGCCTG CCCTTGCCCC ACTCCTGAAT GCACCACATG  1140

CCTCTGTCTC CCCGCTGAGC CCAGGCACTT GCCCAGGCCG CCCTGCAGGA CCACTGCAAT  1200

AAACGCC                                                            1207
```

(2) INFORMATION FOR SEQ ID NO:5:

(i) SEQUENCE CHARACTERISTICS:
(A) LENGTH: 279 amino acids
(B) TYPE: amino acid
(C) STRANDEDNESS: single
(D) TOPOLOGY: linear (vii) IMMEDIATE SOURCE:

(A) LIBRARY: GenBank
(B) CLONE: 1143494

(xi) SEQUENCE DESCRIPTION: SEQ ID NO:5:

```
Met Gln Leu Thr Gln Asp Asp Asp Thr Asp Ala Val Glu Ile Ala Ile
 1               5                  10                  15

Asp Asn Thr Ala Phe Met Asp Glu Phe Phe Ser Glu Ile Glu Glu Thr
            20                  25                  30

Arg Leu Asn Ile Asp Lys Ile Ser Glu His Val Glu Glu Ala Lys Lys
        35                  40                  45

Leu Tyr Ser Ile Ile Leu Ser Ala Pro Ile Pro Glu Pro Lys Thr Lys
    50                  55                  60

Asp Asp Leu Glu Gln Leu Ser Thr Glu Ile Lys Lys Arg Ala Asn Asn
65                  70                  75                  80

Val Arg Asn Lys Leu Lys Ser Met Glu Lys His Ile Glu Glu Asp Glu
                85                  90                  95

Val Arg Ser Ser Ala Asp Leu Arg Ile Arg Lys Ser Gln His Ser Val
            100                 105                 110

Leu Ser Arg Lys Phe Val Glu Val Met Thr Lys Tyr Asn Glu Ala Gln
        115                 120                 125

Val Asp Phe Arg Glu Arg Ser Lys Gly Arg Ile Gln Arg Gln Leu Glu
    130                 135                 140

Ile Thr Gly Lys Lys Thr Thr Asp Glu Glu Leu Glu Glu Met Leu Glu
145                 150                 155                 160

Ser Gly Asn Pro Ala Ile Phe Thr Ser Gly Ile Ile Asp Ser Gln Ile
                165                 170                 175

Ser Lys Gln Ala Leu Ser Glu Ile Glu Gly Arg His Lys Asp Ile Val
            180                 185                 190

Arg Leu Glu Ser Ser Ile Lys Glu Leu His Asp Met Phe Met Asp Ile
        195                 200                 205

Ala Met Leu Val Glu Asn Gln Gly Glu Met Leu Asp Asn Ile Glu Leu
    210                 215                 220

Asn Val Met His Thr Val Asp His Val Glu Lys Ala Arg Asp Glu Ser
225                 230                 235                 240

Lys Lys Ala Val Lys Tyr Gln Ser Gln Ala Arg Lys Lys Leu Ile Ile
                245                 250                 255

Ile Ile Val Leu Val Val Val Leu Leu Gly Ile Leu Ala Leu Ile Ile
            260                 265                 270

Gly Leu Ser Val Gly Leu Asn
        275
```

(2) INFORMATION FOR SEQ ID NO:6:

(i) SEQUENCE CHARACTERISTICS:
(A) LENGTH: 289 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 924268

(xi) SEQUENCE DESCRIPTION: SEQ ID NO:6:

```
Met Lys Asp Arg Leu Glu Gln Leu Lys Ala Lys Gln Leu Thr Gln Asp
 1               5                  10                  15

Asp Asp Thr Asp Glu Val Glu Ile Ala Ile Asp Asn Thr Ala Phe Met
            20                  25                  30
```

-continued

```
Asp Glu Phe Phe Ser Glu Ile Glu Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
        115                 120                 125

Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Ile Val Val Val Val
            260                 265                 270

Val Leu Leu Gly Ile Leu Ala Leu Ile Ile Gly Leu Ser Val Gly Leu
        275                 280                 285

Lys
```

(2) INFORMATION FOR SEQ ID NO:7:

(i) SEQUENCE CHARACTERISTICS:
(A) LENGTH: 355 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 643658

(xi) SEQUENCE DESCRIPTION: SEQ ID NO:7:

```
Pro Arg Trp Thr Leu Phe Ile Ala Ile Leu Ala Ala Gly Val Leu Leu
 1               5                  10                  15

Val Ser Cys Leu Leu Cys Val Ile Cys Cys Tyr Cys His Arg His Arg
            20                  25                  30

His Arg Lys Gln Pro Lys Asp Lys Glu Thr Val Gly Leu Gly Ser Ala
        35                  40                  45

Arg Asn Ser Thr Thr Thr His Leu Val Gln Pro Asp Val Asp Cys Leu
    50                  55                  60

Glu Pro Cys Ser Gly Gly Asp Gln Gln Trp Gly Arg Leu Leu Leu Ser
65                  70                  75                  80
```

-continued

```
Leu Glu Tyr Asp Phe Gly Ser Gln Glu Ile Arg Val Gly Leu Arg Gln
                85                  90                  95

Ala Gly Asn Leu Lys Ala Glu Gly Thr Ala Asp Pro Tyr Ala Trp Val
            100                 105                 110

Ser Val Ser Thr Gln Ser Gly Arg Arg His Glu Thr Lys Val His Arg
        115                 120                 125

Gly Thr Leu Ser Pro Met Phe Glu Glu Thr Cys Cys Phe Leu Val Pro
    130                 135                 140

Pro Ala Glu Leu Pro Lys Ala Thr Leu Lys Val Gln Leu Trp Asp Phe
145                 150                 155                 160

Lys Arg Phe Ser Glu His Glu Pro Leu Gly Glu Leu Gln Leu Pro Leu
                165                 170                 175

Gly Thr Val Asp Leu Gln His Val Leu Glu Ser Trp Tyr Gln Leu Gly
            180                 185                 190

Pro Pro Gly Thr Thr Glu Pro Glu Gln Met Gly Glu Leu Cys Phe Ser
        195                 200                 205

Leu Arg Tyr Val Pro Ser Ser Gly Ser Leu Thr Val Val Val Leu Glu
    210                 215                 220

Ala Arg Gly Leu Asn Pro Gly Leu Ala Glu Ala Tyr Val Lys Ile Gln
225                 230                 235                 240

Leu Met Leu Asn Gln Arg Lys Trp Lys Lys Ser Lys Thr Ser Ser Lys
                245                 250                 255

Lys Gly Thr Thr Thr Pro Tyr Phe Asn Glu Ala Phe Val Phe Leu Val
            260                 265                 270

Pro Val Ser Gln Leu Gln Ser Val Asp Leu Val Leu Ala Val Trp Ala
        275                 280                 285

Arg Gly Leu Gln Leu Arg Thr Glu Pro Val Gly Lys Val Leu Leu Gly
    290                 295                 300

Ser Arg Ala Ser Gly Gln Pro Leu Gln His Trp Ala Asp Met Leu Ala
305                 310                 315                 320

His Ala Arg Arg Pro Ile Ala Gln Trp His His Leu Arg Ser Pro Arg
                325                 330                 335

Glu Val Asp Arg Val Leu Ala Leu Gln Pro Arg Leu Pro Leu Leu Arg
            340                 345                 350

Pro Arg Ser
        355
```

(2) INFORMATION FOR SEQ ID NO:8:

(i) SEQUENCE CHARACTERISTICS:
(A) LENGTH: 422 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 338658

(xi) SEQUENCE DESCRIPTION: SEQ ID NO:8:

```
Met Val Ser Glu Ser His His Glu Ala Leu Ala Ala Pro Pro Val Thr
 1              5                   10                  15

Thr Val Ala Thr Val Leu Pro Ser Asn Ala Thr Glu Pro Ala Ser Pro
            20                  25                  30

Gly Glu Gly Lys Glu Asp Ala Phe Ser Lys Leu Lys Glu Lys Phe Met
        35                  40                  45

Asn Glu Leu His Lys Ile Pro Leu Pro Pro Trp Ala Leu Ile Ala Ile
    50                  55                  60
```

-continued

```
Ala Ile Val Ala Val Leu Leu Val Leu Thr Cys Cys Phe Cys Ile Cys
65                  70                  75                  80

Lys Lys Cys Leu Phe Lys Lys Lys Asn Lys Lys Lys Gly Lys Glu Lys
                85                  90                  95

Gly Gly Lys Asn Ala Ile Asn Met Lys Asp Val Lys Asp Leu Gly Lys
            100                 105                 110

Thr Met Lys Asp Gln Ala Leu Lys Asp Asp Asp Ala Glu Thr Gly Leu
        115                 120                 125

Thr Asp Gly Glu Glu Lys Glu Glu Pro Lys Glu Glu Glu Lys Leu Gly
    130                 135                 140

Lys Leu Gln Tyr Ser Leu Asp Tyr Asp Phe Gln Asn Asn Gln Leu Leu
145                 150                 155                 160

Val Gly Ile Ile Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Phe Glu Thr Lys Val His Arg Lys Thr Leu Asn Pro Val Phe Asn
        195                 200                 205

Glu Gln Phe Thr Phe Lys Val Pro Tyr Ser Glu Leu Gly Gly Lys Thr
    210                 215                 220

Leu Val Met Ala Val Tyr Asp Phe Asp Arg Phe Ser Lys His Asp Ile
225                 230                 235                 240

Ile Gly Glu Phe Lys Val Pro Met Asn Thr Val Asp Phe Gly His Val
                245                 250                 255

Thr Glu Glu Trp Arg Asp Leu Gln Ser Ala Glu Lys Glu Glu Gln Glu
            260                 265                 270

Lys Leu Gly Asp Ile Cys Phe Ser Leu Arg Tyr Val Pro Thr Ala Gly
        275                 280                 285

Lys Leu Thr Val Val Ile Leu Glu Ala Lys Asn Leu Lys Lys Met Asp
    290                 295                 300

Val Gly Gly Leu Ser Asp Pro Tyr Val Lys Ile His Leu Met Gln Asn
305                 310                 315                 320

Gly Lys Arg Leu Lys Lys Lys Lys Thr Thr Ile Lys Lys Asn Thr Leu
                325                 330                 335

Asn Pro Tyr Tyr Asn Glu Ser Phe Ser Phe Glu Val Pro Phe Glu Gln
            340                 345                 350

Ile Gln Lys Val Gln Val Val Val Thr Val Leu Asp Tyr Asp Lys Ile
        355                 360                 365

Gly Lys Asn Asp Ala Ile Gly Lys Val Phe Val Gly Tyr Asn Ser Thr
    370                 375                 380

Gly Ala Glu Leu Arg His Trp Ser Asp Met Leu Ala Asn Pro Arg Arg
385                 390                 395                 400

Pro Ile Ala Gln Trp His Thr Leu Gln Val Glu Glu Glu Val Asp Ala
                405                 410                 415

Met Leu Ala Val Lys Lys
            420
```